US011253463B2

(12) United States Patent
Dobkowski et al.

(10) Patent No.: US 11,253,463 B2
(45) Date of Patent: *Feb. 22, 2022

(54) COSMETIC COMPOSITIONS COMPRISING SILICONE ELASTOMER AND EMOLLIENT

(71) Applicant: Conopco, Inc., Trumbull, CT (US)

(72) Inventors: Brian John Dobkowski, Milford, CT (US); Sheng Meng, Shanghai (CN); Wenhui Song, Shanghai (CN); Xiaoxia Yang, Shanghai (CN); Wei Zhao, Shanghai (CN)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/764,953

(22) PCT Filed: Nov. 19, 2018

(86) PCT No.: PCT/EP2018/081775
§ 371 (c)(1),
(2) Date: May 18, 2020

(87) PCT Pub. No.: WO2019/115169
PCT Pub. Date: Jun. 20, 2019

(65) Prior Publication Data
US 2020/0345619 A1    Nov. 5, 2020

(30) Foreign Application Priority Data
Jan. 8, 2018   (EP) .................................. 18150585

(51) Int. Cl.
*A61K 8/895* (2006.01)
*A61K 8/891* (2006.01)
*A61K 8/92* (2006.01)
*A61Q 17/04* (2006.01)
*A61Q 19/00* (2006.01)

(52) U.S. Cl.
CPC .............. *A61K 8/895* (2013.01); *A61K 8/891* (2013.01); *A61K 8/922* (2013.01); *A61Q 17/04* (2013.01); *A61Q 19/007* (2013.01)

(58) Field of Classification Search
CPC ........ A61K 8/585; A61K 8/891; A61Q 19/00; A61Q 17/04
See application file for complete search history.

(56) References Cited

U.S. PATENT DOCUMENTS

| 3,525,709 A | 8/1970 | Somerville et al. |
| 5,760,116 A | 6/1998 | Kilgour et al. |
| 6,184,277 B1 | 2/2001 | Bara |
| 6,221,979 B1 | 4/2001 | Lin et al. |
| 6,183,766 B1 | 6/2001 | Sine et al. |
| 2002/0022040 A1 | 2/2002 | Robinson et al. |
| 2002/0037951 A1 | 3/2002 | Kilgour et al. |
| 2003/0049212 A1 | 3/2003 | Robinson et al. |
| 2004/0044121 A1 | 3/2004 | Kadlec et al. |
| 2004/0234478 A1 | 11/2004 | Clapp |
| 2006/0239950 A1 | 10/2006 | Mohammadi et al. |
| 2008/0206172 A1* | 8/2008 | Mohammadi ............ A61K 8/33 424/60 |
| 2009/0137534 A1* | 5/2009 | Chaudhuri ........... A61K 31/203 514/159 |
| 2010/0135916 A1 | 6/2010 | Courel et al. |
| 2010/0196292 A1 | 8/2010 | Carson et al. |
| 2010/0322877 A1 | 12/2010 | Zofchak et al. |
| 2013/0045260 A1* | 2/2013 | Yamaguchi ............ A61K 8/895 424/401 |
| 2013/0079368 A1* | 3/2013 | Omura .................. A61Q 19/007 514/315 |
| 2014/0154294 A1* | 6/2014 | Finjan ................... A61K 8/895 424/401 |

(Continued)

FOREIGN PATENT DOCUMENTS

| DE | 102015224498 | 6/2017 |
| EP | 0850640 | 1/1998 |
| EP | 0940423 | 9/1999 |
| EP | 1002825 | 5/2000 |
| EP | 1097968 | 5/2001 |
| GB | 1153721 | 5/1969 |
| GB | 2420076 | 5/2006 |
| GB | 2453952 | 4/2009 |

(Continued)

OTHER PUBLICATIONS

Search Report and Written Opinion in PCTEP2018081775; dated Jan. 24, 2019.

(Continued)

*Primary Examiner* — Mark V Stevens
(74) *Attorney, Agent, or Firm* — Stephanie Huang

(57) ABSTRACT

Disclosed is a cosmetic composition comprising (i) 1 to 30 wt % of a non-hydrocarbon emollient; and (ii) 2 to 60 wt % of a blend of silicone elastomer gel of the Formula (I) and solvent; wherein the solvent for the silicone elastomer gel is selected from cyclic or linear polydimethylsiloxanes; wherein the w/w ratio of the amount of the non-hydrocarbon emollient to the combined amounts of the silicone elastomer gel and said solvent is from 1:50 to 1:1 and where the amount of the non-hydrocarbon emollient is less than the amount of the silicone elastomer gel; and wherein the composition comprises less than 2 wt % capric caprylic triglycerides and less than 5 wt % crosslinked elastomeric silicone polyether, wherein said non-hydrocarbon emollient is an alkenyl or alkyl ester of a C10-20 fatty acid, an ether-ester, a polyhydric alcohol ester, a wax ester, a mono-, di- or triglyceride, a sterol ester, a fatty alcohol, a fatty acid, lanolin or its derivative, wax ester, a phospholipid, beeswax or a sterol.

15 Claims, No Drawings

(56) References Cited

U.S. PATENT DOCUMENTS

| | | |
|---|---|---|
| 2015/0164774 A1 | 6/2015 | Masatomi et al. |
| 2015/0274972 A1 | 10/2015 | Mateu et al. |
| 2016/0089312 A1 | 3/2016 | Dique-Mouton et al. |
| 2016/0194455 A1 | 7/2016 | Mateu et al. |

FOREIGN PATENT DOCUMENTS

| | | |
|---|---|---|
| JP | 2016150252 | 8/2016 |
| WO | WO0007184 | 2/2000 |
| WO | WO0114458 | 3/2001 |
| WO | WO0203930 | 1/2002 |
| WO | WO0203952 | 1/2002 |
| WO | WO2004020527 | 3/2004 |
| WO | WO2006110271 | 10/2006 |
| WO | WO2006115816 | 11/2006 |
| WO | WO2007054492 | 5/2007 |
| WO | WO2009054931 | 4/2009 |
| WO | WO2009138305 | 11/2009 |
| WO | WO2010087962 | 8/2010 |
| WO | WO2013161429 | 10/2013 |
| WO | WO2014058856 | 4/2014 |
| WO | WO2014170865 | 10/2014 |
| WO | WO2017144530 | 8/2017 |
| WO | WO2017144531 | 8/2017 |
| WO | WO-2017144531 A1 * | 8/2017 ............ A61K 8/891 |
| WO | WO2017211525 | 12/2017 |
| WO | WO2017211580 | 12/2017 |

OTHER PUBLICATIONS

Search Report and Written Opinion in EP18150585; dated Mar. 9, 2018.

IPRP2 in PCTEP2018081775; dated Dec. 12, 2019.

* cited by examiner

COSMETIC COMPOSITIONS COMPRISING SILICONE ELASTOMER AND EMOLLIENT

CROSS REFERENCE TO RELATED APPLICATIONS

The present application is a U.S. National Phase Application under 35 U.S.C. § 371 of International Application No. PCT/EP2018/081775, filed on Nov. 19, 2018, which claims priority to International Application No. PCT/CN2017/115580, filed on Dec. 12, 2017, and European Patent Application No. 18150585.0, filed on Jan. 08, 2018, the contents of which are incorporated herein in their entireties.

TECHNICAL FIELD OF THE INVENTION

The invention concerns a cosmetic composition, especially a cosmetic composition comprising silicone elastomer and non-hydrocarbon emollient.

BACKGROUND OF THE INVENTION

Emollients are used widely in cosmetics for care and protection of the skin. Emollients are the materials used for prevention of or relief from dryness. Dry skin is generally rough and flaky, less flexible than normal and is often found to have fissures or micro fissures.

Emollients are often included in cosmetics meant for hand-&-body care. In some cases, it is the intention of formulators to increase the amount of emollients beyond the normal or usual range. However, an increase may not be feasible easily because the formulations may no longer remain stable. In particular, the formulations might develop and show evident signs of phase-separation upon exposure to high temperature which is usually around 50° C. However, reputed cosmetic brands need to ensure that their products are stable.

Silicone elastomers are included in cosmetic compositions to improve sensorial properties. The term silicone elastomer means cross-linked silicone polymer which swell significantly in a solvent forming a space-filling material which behaves as a visco-elastic soft solid. Generally, the silicone elastomers are dosed in the form of a blend of the elastomer with a suitable solvent such a cyclic or linear silicone solvent.

U.S. 2004234478 AA (P&G) discloses personal care compositions containing a dispersed oil phase, a silicone elastomer and an aqueous phase. The wash-off compositions are able to deposit oil and silicone elastomer onto all keratinous surfaces while improving the skin feel. The elastomer is dispersed in the structured oil which allows for co-deposition of oil and elastomer.

U.S. Pat. No. 6,221,979B (Dow Corning, 2001) discloses cosmetic compositions comprising a blend of (i) a cross-linked elastomeric silicone polyether and (ii) a crosslinked elastomeric silicone containing alkyl groups having 3 to 40 carbon atoms. The new composition is used for preparing water-in-oil emulsions and clear solutions containing an oil(s) or an oil-soluble active ingredient. This blend is used to compatibilise organic oils which are as polar as sunflower oil. It is disclosed that the benefits cannot be achieved using only one elastomer.

U.S. 20060239950 A1 (E L Management Co) discloses that combining a specific emollient system with aqueous dispersion of a particulate silicone elastomer can stabilize the composition even with a relatively high amount of the dispersion present in the final composition. The compositions help reduce the appearance of lines and wrinkles.

GB200520896 A (The Boots Co) discloses a cosmetic composition for cleansing and smoothing effect having 30 to 75 wt % oil phase, 1 to 20 wt % surfactant, 0.01 to 20 wt % elastomer and 2 to 40 wt % aqueous phase. The preferred oil phase is caprylic/capric triglyceride and the elastomer is dimethicone crosspolymer. The oil phase is more than the elastomer.

Unpublished application PCT/EP2017/061001 (Unilever) discloses cosmetic compositions which comprise a silicone elastomer of a particular structure and a hydrocarbon emollient. Usually such elastomers and emollients are believed to be incompatible but the elastomer contains organic side chains which solves the problem.

The present inventors have now found unexpectedly found that cosmetic compositions comprising a silicone elastomer gel having a particular structure as defined herein and a non-hydrocarbon emollient, are stable for prolonged period. This observation provides a reliable method to formulate cosmetic compositions comprising non-hydrocarbon emollients in more than the usual or the standard amounts.

SUMMARY OF THE INVENTION

In accordance with a first aspect is disclosed a cosmetic composition comprising:
(i) 1 to 30 wt % of a non-hydrocarbon emollient; and
(ii) 2 to 60 wt % of a blend of silicone elastomer gel of the Formula (I) and solvent;
wherein the solvent for the silicone elastomer gel is selected from cyclic or linear polydimethylsiloxanes;
wherein the w/w ratio of the amount of the non-hydrocarbon emollient to the combined amounts of the silicone elastomer gel and said solvent is from 1:50 to 1:1 and where the amount of the non-hydrocarbon emollient is less than the amount of the silicone elastomer gel;

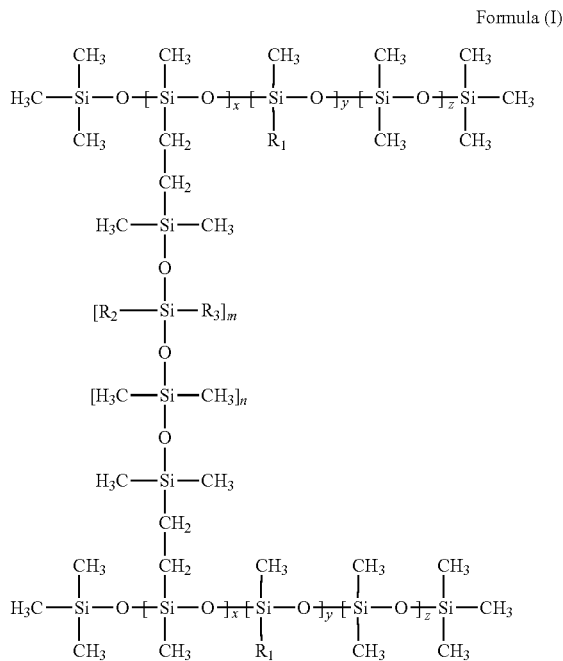

Formula (I)

wherein:
each $R_1$ is independently, $C_{1-36}$ alkyl chain, preferably $C_{8-18}$ alkyl chain;
each $R_2$ is independently, phenyl or $CH_3$;
each $R_3$ is phenyl; and
each x is independently an integer from 3 to 100, preferably from 3 to 20; each y is independently an integer from 1 to 100, preferably from 1 to 20; each z is independently an integer from 1 to 100, preferably from 6 to 50; each m is independently an integer from 1 to 100, preferably from 5 to 30; and each n is independently an integer from 4 to 1000, preferably from 40 to 500, and wherein the composition comprises less than 2 wt % capric caprylic triglycerides and less than 5 wt % crosslinked elastomeric silicone polyether, wherein said non-hydrocarbon emollient is an alkenyl or alkyl ester of a $C_{10-20}$ fatty acid, an ether-ester, a polyhydric alcohol ester, a wax ester, a mono-, di- or triglyceride, a sterol ester, a fatty alcohol, a fatty acid, lanolin or its derivative, wax ester, a phospholipid, beeswax or a sterol.

In accordance with a second aspect is disclosed a packaged personal care product comprising the cosmetic composition of the first aspect of this invention.

In accordance with a third aspect is a method of moisturising the skin comprising a step of topically applying a cosmetic composition of the first aspect to the skin.

In accordance with a fourth aspect is disclosed use of a composition of the first aspect for moisturising the skin.

All other aspects of the present invention will more readily become apparent upon considering the detailed description and examples which follow.

Except in the examples, or where otherwise explicitly indicated, all numbers in this description indicating amounts of material or conditions of reaction, physical properties of materials and/or use may optionally be understood as modified by the word "about".

All amounts are by weight of the cosmetic composition, unless otherwise specified.

It should be noted that in specifying any ranges of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

DETAILED DESCRIPTION

By a cosmetic composition is meant a composition for external application in the form of a leave-on or wash-off format meant for cleaning or care of the skin. Such a composition includes any product applied to a human body for improving appearance, cleansing or general aesthetics. The compositions in accordance with the invention are rinse off-products. Alternatively, and more preferably they are leave-on products. The composition of the present invention may be in the form of a liquid, lotion, cream, foam or gel, or toner, or applied with an implement or via a face mask, pad or patch. "Skin" as used herein is meant to include skin on the face and body (e.g., neck, chest, back, arms, underarms, hands, legs, buttocks and scalp).

The Non-Hydrocarbon Emollient

The compositions in accordance with this invention comprise 1 to 30 wt % of a non-hydrocarbon emollient. Hydrocarbon, as used herein, refers to an organic compound consisting entirely of hydrogen and carbon. Such hydrocarbons include cyclic hydrocarbons, straight chain aliphatic hydrocarbons (saturated or unsaturated), and branched chain aliphatic hydrocarbons (saturated or unsaturated). Illustrative examples include mineral oil, wax and petrolatum (such as petroleum jelly).

The non-hydrocarbon emollient is an alkenyl or alkyl ester of a $C_{10-20}$ fatty acid, an ether-ester, a polyhydric alcohol ester, a wax ester, a mono-, di- or triglyceride, a sterol ester, a fatty alcohol, a fatty acid, lanolin or its derivative, wax ester, a phospholipid, beeswax or a sterol.

More preferably the non-hydrocarbon emollient is a triglyceride. Further preferably the triglyceride is one or more of wheatgerm oil, apricot kernel oil, avocado oil, sunflower seed oil, arnica oil, evening primrose oil, jojoba oil, coconut oil, palm kernel oil, groundnut oil, safflower oil, cotton seed oil, rape seed oil, palm oil, almond oil, rice bran oil, castor oil, macadamia oil or shea butter.

Suitable examples of preferred non-hydrocarbon emollients are as follows:
acetoglyceride esters: example acetylated monoglycerides;
alkyl esters: examples methyl, isopropyl, and butyl esters of fatty acids; hexyl laurate, isohexyl laurate, isopropyl myristate, isopropyl palmitate, decyl oleate, isodecyl oleate, hexadecyl (isocetyl) stearate, diisopropyl adipate, diisohexyl adipate, dihexadecyl adipate, diisopropyl sebacate, lauryl lactate, myristyl lactate, and cetyl lactate;
alkenyl esters: example oleyl myristate, oleyl stearate, and oleyl oleate;
fatty acids: example lauric, myristic, palmitic, stearic, isostearic, hydroxystearic, oleic, linoleic, linolenic, gamma.-linolenic, ricinoleic, arachidic, behenic, erucic, and lanolin acids;
polyhydric alcohol esters: example ethylene glycol mono and di-fatty acid esters, diethylene glycol mono- and di-fatty acid esters, polyethylene glycol (200-6000)

mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters;

fatty alcohols: example lauryl, myristyl, cetyl, hexadecyl (isocetyl), stearyl, isostearyl, hydroxystearyl, oleyl, ricinoleyl, behenyl and erucyl alcohols, and 2-octyl dodecanol;

fatty alcohol ethers: example ethoxylated lauryl, cetyl, stearyl, isostearyl, oleyl, and lanolin alcohols; and cholesterol; propoxylated cetyl, oleyl, and lanolin alcohols; and polypropylene-15-stearyl ether;

ether-esters: example fatty acid esters of ethoxylated fatty alcohols;

lanolin and lanolin derivatives: example lanolin, lanolin oil, lanolin wax, lanolin alcohols, lanolin fatty acids and acetylated lanolin derivatives;

wax esters: example beeswax, spermaceti, myristyl myristate, stearyl stearate;

beeswax derivatives: example polyoxyethylene sorbitol beeswax. These are reaction products of beeswax with ethoxylated sorbitol of varying ethylene oxide content, forming a mixture of ether-esters;

vegetable waxes: example carnauba, candelilla;

phopholipids: example lecithin and derivatives; and, sterols: example cholesterol and cholesterol fatty acid esters.

More preferably the compositions of the invention comprise from 1.5 to 20 wt %, most preferably from 2 to 10 wt % of the non-hydrocarbon emollient.

The cosmetic compositions of the present invention comprises less than 2 wt % capric caprylic triglyceride, more preferably less than 1 wt % and most preferably less than 0.5 wt %.

The silicone Elastomer Gel

Silicone elastomer gel, as used herein, means cross-linked silicone polymer gel that swells significantly in a solvent forming a space filling material which behaves as a viscoelastic soft solid. Alkyl mole content as used herein, means the ratio of moles of alkyl substituted dimethicone units to the total moles of dimethicone units per mole of silicone elastomer unit, unless otherwise specified. The term "gel" as used herein means that the silicone elastomer in the cosmetic compositions of the invention is not particulate.

Phenyl mole content as used herein, means the ratio of moles of phenyl substituted dimethicone units to the total number of dimethicone units per mole of silicone elastomer unit, unless otherwise specified.

The silicone elastomer gel has the following formula:

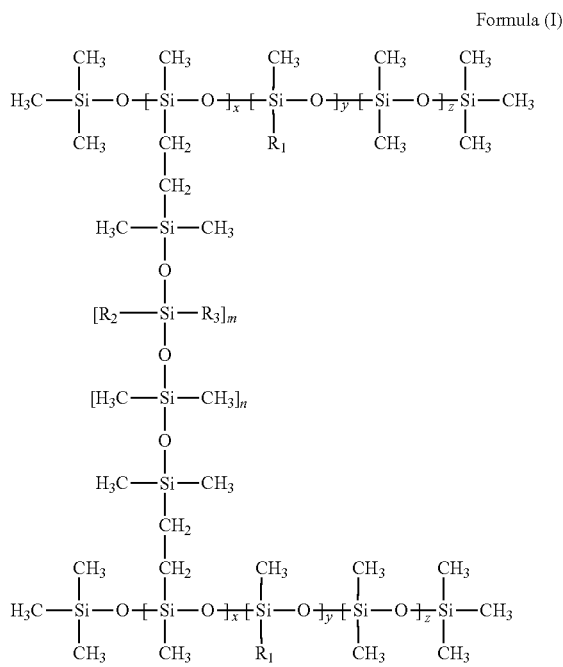

Formula (I)

wherein:

each $R_1$ is independently, $C_{1-36}$ alkyl chain, preferably $C_{8-18}$ alkyl chain;

each $R_2$ is independently, phenyl or $CH_3$;

each $R_3$ is phenyl; and each x is independently an integer from 3 to 100, preferably from 3 to 20; each y is independently an integer from 1 to 100, preferably from 1 to 20; each z is independently an integer from 1 to 100, preferably from 6 to 50; each m is independently an integer from 1 to 100, preferably from 5 to 30; and each n is independently an integer from 4 to 1000, preferably from 40 to 500.

Silicone elastomer gels suitable for use in the cosmetic compositions of the present invention are functional silicone elastomers that are modified by grafting functional groups onto the backbones of elastomers. It is preferred that the silicone elastomer is alkyl modified, phenyl modified or more preferably dual (alkyl and phenyl) modified silicone elastomers.

Alkyl modified silicone elastomer gels may be prepared from the reaction of a) a silicone-hydride containing polysiloxane; b) an alkene; and c) a vinyl-terminated dimethylpolysiloxane by using a hydrosilylation catalyst. In the reaction, the alkene reacts with the silicone-hydride containing polysiloxane to form an alkyl modified polysiloxane, which reacts with the vinyl-terminated dimethylpolysiloxane to form the alkyl modified silicone elastomer.

When the silicone elastomer is alkyl modified or dual modified as disclosed earlier, it is preferred that the alkyl mole content is 0.01 to 0.99, more preferably from 0.02 to 0.20.

Preferably the silicone elastomer has the following general formula:

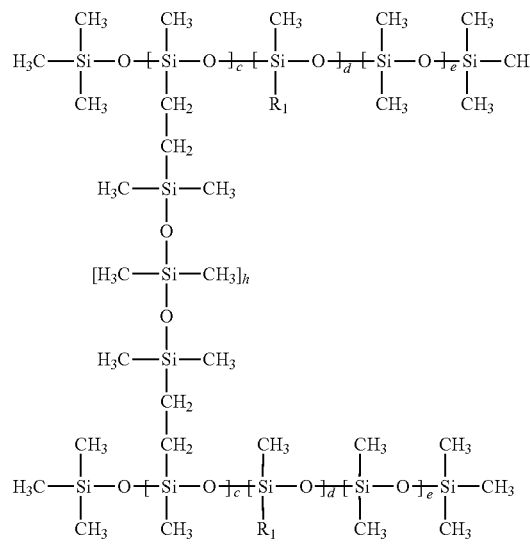

(II)

As an alternative to the structure disclosed as (II) above, a phenyl modified functional silicone elastomer has the following preferred general formula:

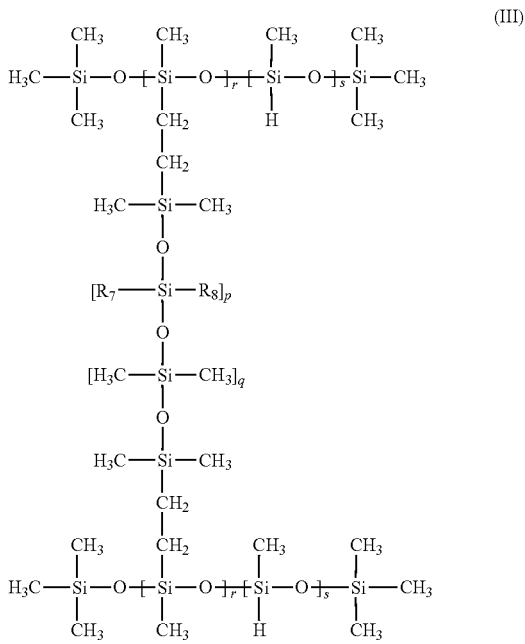

(III)

wherein:

each $R_4$ is independently $C_{1-36}$ alkyl chain, preferably $C_{8-18}$; and each c is independently an integer from 3 to 100, preferably from 3 to 20; each d is independently an integer from 1 to 100, preferably from 1 to 20; each e is independently an integer from 1 to 100, preferably from 6 to 50; and each h is independently an integer from 4 to 1000, preferably from 40 to 500.

Phenyl modified silicone elastomer gel may be prepared from the reaction of a silicone-hydride containing polysiloxane; and a vinyl-terminated dimethyl phenyl polysiloxane by using a hydrosilylation catalyst. Phenyl mole content as used herein, means the ratio of moles of phenyl substituted dimethicone units to the total moles of dimethicone units of the vinyl-terminated dimethyl phenyl polysiloxane. Preferably the phenyl content of the vinyl-terminated dimethyl phenyl polysiloxane is 1 to 50%, more preferably 3 to 30% and most preferably from 7 to 15%. Preferably the phenyl mole content of the phenyl modified silicone elastomer is typically in the range from 0.01 to 0.50, more preferably from 0.03 to 0.34.

wherein:

each $R_7$ is independently phenyl or $CH_3$;

each $R_8$ is phenyl; and each r is independently an integer from 3 to 100, preferably from 3 to 20; each s is independently an integer from 2 to 200, preferably from 7 to 70; each p is independently an integer from 1 to 100, preferably from 5 to 30; and each q is independently an integer from 4 to 1000, preferably from 40 to 500.

Dual (alkyl and phenyl) modified silicone elastomer may be prepared from the reaction of a silicone-hydride containing polysiloxane; an alkene; and a vinyl-terminated dimethyl phenyl polysiloxane by using a hydrosilylation catalyst.

The alkyl mole content of the dual (alkyl and phenyl) modified silicone elastomer is preferably in the range of 0.01 to 0.99, more preferably from 0.02 to 0.20.

The phenyl mole content of the dual (alkyl and phenyl) modified silicone elastomer is preferably in the range of 0.01 to 0.50, preferably from 0.03 to 0.34.

It is preferred that the dual (alkyl and phenyl) modified silicone elastomer has the general formula:

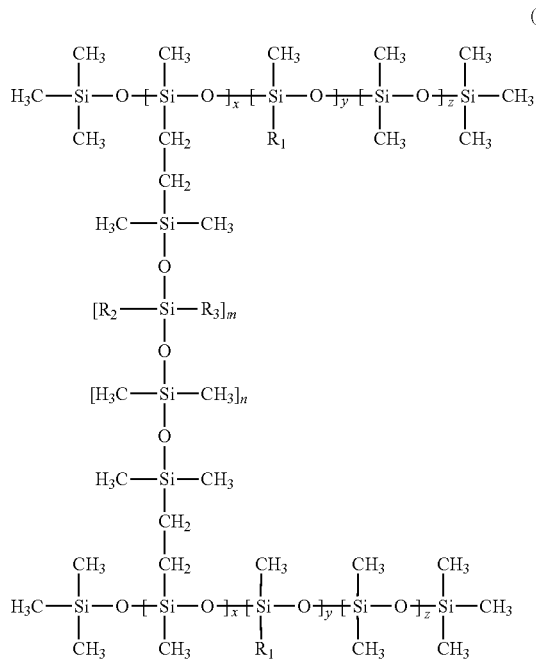

(IV)

wherein:

each $R_1$ is independently $C_{4-36}$ alkyl chain, preferably $C_{8-18}$;

each $R_2$ is independently phenyl or $CH_3$;

each $R_3$ is independently phenyl; and each x is independently an integer from 3 to 100, preferably from 3 to 20; each y is independently an integer from 1 to 100, preferably from 1 to 20; each z is independently an integer from 1 to 100, preferably from 6 to 50; each m is independently an integer from 1 to 100, preferably from 5 to 30; and each n is independently an integer from 4 to 1000, preferably from 40 to 500.

Further, it is particularly preferred that in the cosmetic compositions of the present invention, the silicone elastomer is of the Formula (IV) (i.e., the dual functional elastomer)

The compositions of the present invention comprise less than 5 wt % crosslinked elastomeric silicone polyether, more preferably less than 2 wt %, most preferably less than 1 wt %. The crosslinked elastomeric silicone polyethers and method of preparing such elastomers are disclosed in U.S. Pat. No. 5,811,487 B1.

The compositions of the present invention comprise a solvent for the silicone elastomer gel selected from cyclic or linear polydimethylsiloxanes.

Generally, silicone elastomer gels are made available and used in the form of a blend of the silicone elastomer and the solvent which is a dispersion of the silicone elastomer in the solvent. The blends of silicone elastomer and solvent are cross-linked gels that can be prepared by hydrosilylation reaction. The reaction involves low levels of catalyst, usually platinum derivatives, and is generally run into an adequate solvent. Silicone-hydride (SiH) containing silicone polymers are reacted with di-vinyl materials to link independent silicone chains.

The solvent for the elastomer is selected from cyclic or linear polydimethylsiloxanes. Preferably the cyclic polydimethylsiloxane is octamethylcyclotetrasiloxane, decamethylcyclopentasiloxane or dodecamethylcyclohexasiloxane. Preferably the linear polydimethylsiloxane is trimethicone or dimethicone. Preferably the linear polydimethylsiloxane is a volatile oil. Particularly preferred volatile oils are linear siloxanes containing from 3 to 9 silicon atoms. Alternatively, it is non-volatile. Examples of commercially available volatile solvents include oils having preferred designations 344, 345, 244, 245 and 246 from Dow corning Corporation. The more cyclic polydimethylsiloxane is decamethylcyclopentasiloxane, which is made commercially available, for example, from Dow Corning Corporation under the trade name DC 245.

Under a shear force the elastomer swells in the presence of the solvent. The volatile silicone oil as per the present invention has vapor pressure of 2.6 to 1400 Pa at 25° C. Preferably the silicone elastomer and the solvent for said elastomer are present in the form of a blend of which the silicone elastomer forms 1 to 70 parts by weight, more preferably from 5 to 50 parts by weight, most preferably from 8 to 30 parts by weight. The reference to parts by weight here is with regard to the blend and not the cosmetic composition which comprises such a blend. In the finished product, for example, in a skincare lotion, it may not be possible to identify that the elastomer and the solvent for the elastomer were introduced/added together as a blend but usually when the silicone elastomer is a gel and the solvent is also present in the concerned composition, that itself may serve as an indication that when the composition was prepared, the elastomer and the solvent were co-dosed and the elastomer is in the form of a gel, as opposed to particulate elastomers which might permit the introduction of the elastomer as such in the form of particles. When the elastomer and the solvent for the elastomer are introduced as a blend, the formulation scientist needs to know the solids content of the blend (e.g., 65% solids, 70% solids) so that a calculated amount of the blend can be added to the composition to ensure that the composition contains a desired amount of the elastomer.

The compositions of the present invention comprise 2 to 60 wt %, more preferably 2 to 40 wt % and most preferably 5 to 30 wt % blend of the silicone elastomer gel and the solvent for the elastomer.

The w/w ratio of the amount of the non-hydrocarbon emollient to the combined amounts of the silicone elastomer gel and said solvent is from 1:50 to 1:1 and more preferably from 1:10 to 1:1.2. Further, the amount of the non-hydrocarbon emollient is less than the amount of the silicone elastomer gel. It has been observed that this feature is necessary to ensure that the emollient, e.g., an oil, is stabilised in the composition by the elastomer and not the other way around.

Other Ingredients

The personal care composition of the invention may be in any form including toners, lotions, creams, mousses, serum or gel that is suitable for topical application to the skin. The cosmetic composition can be either a leave-on or a rinse-off product, preferably a leave-on product, especially a skin care product including skin lotions and skin creams.

The cosmetic composition of the present invention may further comprise 0.1 to 10 wt % of a hydrocarbon emollient. Suitable emollients include wax, cyclic hydrocarbons, straight chain aliphatic hydrocarbons (saturated or unsaturated), and branched chain aliphatic hydrocarbons (saturated or unsaturated).

The cosmetic compositions of the invention preferably comprise a cosmetically acceptable carrier. The carrier may be a liquid or solid material. Typically, carrier forms 10 to 99.9%, more preferably 20 to 95%, most preferably 40 to 85% of the composition. Suitable carrier classes include water, silicones other than the silicone which are covered by the silicone elastomer gel of the Formula (I) and the solvent for the silicone elastomer gel; polyhydric alcohols, hydrocarbons, and thickening powders.

In one aspect the cosmetic compositions of the invention are anhydrous. Anhydrous, as used herein, refers to a composition comprises less than 1.5% by weight of water, preferably less than 1.0%.

Alternatively and more preferably the compositions of the invention comprise 10 to 70 wt %, more preferably 10 to 50 wt % and most preferably 10 to 30 wt % water.

Further preferably the compositions of the invention comprise a skin lightening agent. The skin lightening agent is preferably chosen from one or more of a vitamin B3 compound or its derivative e.g. niacin, nicotinic acid or niacinamide or other well known skin lightening agents e.g. adapalene, aloe extract, ammonium lactate, anethole derivatives, apple extract, arbutin, azelaic acid, kojic acid, bamboo extract, bearberry extract, bletilla tuber, bupleurum falcatum extract, burnet extract, butyl hydroxy anisole, butyl hydroxy toluene, citrate esters, Chuanxiong, Dang-Gui, deoxyarbutin, 1,3-diphenyl propane derivatives, 2,5-dihydroxybenzoic acid and its derivatives, 2-(4-acetoxyphenyl)-1,3-dithane, 2-(4-hydroxyphenyl)-1,3-dithane, ellagic acid, escinol, estragole derivatives, Fadeout® (Pentapharm), Fangfeng, fennel extract, ganoderma extract, gaoben, Gatuline Whitening (Gattlefosse), genistic acid and its derivatives, glabridin and its derivatives, gluco pyranosyl-1-ascorbate, gluconic acid, glycolic acid, green tea extract, 4-hydroxy-5-methyl-3[2H]-furanone, hydroquinone, 4-hydroxyanisole and its derivatives, 4-hydroxy benzoic acid derivatives, hydroxycaprylic acid, inositol ascorbate, lemon extract, linoleic acid, magnesium ascorbyl phosphate, Melawhite® (Pentapharm), morus alba extract, mulberry root extract, 5-octanoyl salicylic acid, parsley extract, phellinus linteus extract, pyrogallol derivatives, 2,4-resorcinol derivatives, 3,5-resorcinol derivatives, rose fruit extract, salicylic acid, Song-Yi extract, 3,4,5-trihydroxybenzyl derivatives, tranexamic acid, vitamins like vitamin B6, vitamin B12, vitamin C, vitamin A, dicarboxylic acids, resorcinol derivatives, extracts from plants viz. rubia and symplocos, hydroxycarboxylic acids like lactic acid and their salts e.g. sodium lactate, and mixtures thereof. Vitamin B3 compound or its derivative e.g. niacin, nicotinic acid or niacinamide are the more preferred skin lightening agent as per the invention, most preferred being niacinamide. Niacinamide, when used, is preferably 0.1 to 10 wt %, more preferably 0.2 to 5 wt %.

The compositions may further preferably comprise one or more organic sunscreens. A wide variety of organic sunscreen agents are suitable for use in combination with the essential ingredients of this invention. Suitable UV-A/UV-B sunscreen agents include, 2-hydroxy-4-methoxybenzophenone, octyldimethyl p-aminobenzoic acid, digalloyltrioleate, 2,2-dihydroxy-4-methoxybenzophenone, ethyl-4-(bis(hydroxypropyl)) aminobenzoate, 2-ethylhexyl-2-cyano-3,3-di phenylacrylate, 2-ethylhexylsalicylate, glyceryl p-aminobenzoate, 3,3,5-trimethylcyclohexylsalicylate, methylanthranilate, p-dimethyl-aminobenzoic acid or aminobenzoate, 2-ethylhexyl-p-dimethyl- amino-benzoate, 2-phenylbenzimidazole-5-sulfonic acid, 2-(p-dimethylaminophenyl)-5-sulfonicbenzoxazoic acid, 2-ethylhexyl-p-methoxycinnamate, butylmethoxydibenzoylmethane, 2-hydroxy-4-methoxybenzophenone, octyldimethyl-p-aminobenzoic acid and mixtures thereof. The most suitable organic sunscreens are 2-ethylhexyl-p-methoxycinnamate, butylmethoxydibenzoylmethane or a mixture thereof.

A safe and effective amount of organic sunscreens is 0.1 to 10 wt %, more preferably from 0.1 to 5 wt % of the organic sunscreen agent.

Other materials which can be included in the cosmetically acceptable carrier include humectants, thickeners and powders. Examples of each of these types of material, which can be used singly or as mixtures, are as follows:

Humectants include those of the polyhydric alcohol-type. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, glycerol, ethoxylated glycerol, propoxylated glycerol and mixtures thereof. The amount of humectant may range, for example, anywhere from 0.5 to 50%, more preferably between 1 and 15% by weight of the composition. Most preferred is glycerol (also known as glycerin). Amounts of glycerin may range, for example, from 0.5% to 50%, more preferably from 1 to 35%, optimally from 2 to 15% by weight of the composition.

A variety of thickening agents may be included in the compositions. Illustrative but not limiting are stearic acid, Acrylamide/Sodium Acryloyldimethyltaurate Copolymer (Aristoflex® AVC), Hydroxyethyl Acrylate/Sodium Acryloyldimethyltaurate Copolymer, Aluminum Starch Octenyl Succinate, Polyacrylates (such as Carbomers including Carbopol® 980, Carbopol® 1342, Pemulen TR-2® and the Ultrez® thickeners), Polysaccharides (including xanthan gum, guar gum, pectin, carageenan and sclerotium gums), celluloses (including carboxymethyl cellulose, ethyl cellulose, hydroxyethyl cellulose and methyl hydroxymethyl cellulose), minerals (including talc, silica, alumina, mica and clays, the latter being represented by bentonites, hectorites and attapulgites), magnesium aluminum silicate and mixtures thereof. Amounts of the thickeners may range, for example, from 0.05 to 10 wt %, more preferably from 0.3 to 2 wt % by weight of the composition.

Powders include chalk, talc, Fuller's earth, kaolin, starch, gums, colloidal silica sodium polyacrylate, tetraalkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose and ethylene glycol monostearate.

The cosmetic compositions of the invention may further comprise other ingredients which are common in the art to enhance physical properties and performances. Suitable ingredients include, but are not limited to opacifiers, binders, colorants and pigments, pH adjusting agents, preservatives, optics, perfumes, viscosity modifiers, biological additives, buffering agents, conditioners, natural extracts, essential oils and skin benefit agents including anti-inflammatory agents, cooling agents, antiperspirant agents, anti-aging agents, anti-acne agents, anti-microbial agents and antioxidants.

A wide variety of packaging can be employed to store and deliver the cosmetic compositions. Packaging is often dependent upon the type of personal care end-use. For instance, leave-on skin lotions and creams, shampoos, hair conditioners and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively, of the compositions of the invention may be delivered as a stick formulation in a container with propel-repel mechanism where the stick moves on a platform towards a dispensing orifice. Metallic cans pressurized by a propellant and having a spray nozzle serve as packaging for antiperspirants, shave creams and other sprayable personal care products.

In accordance with another aspect is disclosed a method of moisturizing the skin comprising a step of topically applying a cosmetic composition of the first aspect to the skin. Preferably the method is non-therapeutic. By non-therapeutic is meant that the method is for cosmetic purpose. Alternatively the method is therapeutic in nature.

In accordance with another aspect is disclosed use of a cosmetic composition of the first aspect for moisturising the skin. Preferably the use is for non-therapeutic purpose. By non-therapeutic is meant that the use is for cosmetic purpose. Alternatively the use is therapeutic in nature.

The following examples are provided to facilitate an understanding of the present invention. The examples are not provided to limit the scope of the claims.

EXAMPLES

Example 1

Preparation of a Blends of Silicone Elastomer Gel and a Solvent for the Elastomer Materials Silicone-hydride containing polysiloxane (Andisil XL-10), vinyl-terminated dimethylpolysiloxane (Andisil VS-200), vinyl-terminated dimethyl diphenyl polysiloxane (Andisil SF-2430) were purchased from AB Specialty Silicones.

Decamethylcyclopentasiloxane (DC245) was purchased from Dow Corning Corporation. Platinum catalyst is platinum (0)-1,3-divinyl-1,1,3,3-tetramethyldisiloxane complex solution-in xylene from Sigma Aldrich. All the chemicals were used as received without further purification.

Solids content, as used herein, refers to the weight percentage of silicone elastomers in the blend of silicone elastomer and the solvent.

Preparation of a Dual Functional Silicone Elastomer (as in Formula IV) and DC 245-Blend 1.02 g Andisil XL-10, 0.94 g dodecene and 4 g DC245 were mixed and stirred in a vial, followed by the addition of 2 µL platinum complex catalyst. The mixture was stirred at 60° C. for 30 minutes. Then the reaction mixture was transferred to a flask. 40 g DC245, 20 g Andisil SF-2430 and 6 µL platinum complex catalyst were added to the mixture and the mixture was kept at 60° C. with the reflux of water and stirred at 200 rpm for 4 hours. This led to the formation of a silicone elastomer gel in the solvent which could be diluted to different solids contents at 60° C. after the reaction was complete. This elastomer was termed as (DSE).

Preparation of a Non-Functional Silicone Elastomer and DC245-Blend 0.382 g Andisil XL-10, 12 g Andisil VS-200 and 70 g DC245 were mixed in a flask. 25 µL of platinum complex catalyst was added and the reaction mixture was kept at 45° C. with the reflux of water and stirred at 200 rpm for 5 hours. This led to a silicone elastomer gel which could be diluted to different solids content at 45° C. after the reaction was complete. This elastomer was termed as (NSE)

Method

Each blend as described above was diluted to solids content of 14.5%. The elastomer formed 14.5 parts by weight of the concerned blend.

Cosmetic compositions in the form of creams were prepared by using the blends (as described above) and varying amount of non-hydrocarbon emollients as further described hereinafter.

Details of the compositions comprising sunflower seed oil as the non-hydrocarbon emollient are shown in Table 1. Details of the compositions comprising macadamia oil as the non-hydrocarbon emollient are shown in Table 2. All ingredients are expressed by weight percent by the total composition, and as level of active ingredient, except the silicone elastomer blend and KSG-18A.

TABLE 1

| Ingredients | Composition Ref Code and wt % | | | | |
|---|---|---|---|---|---|
| | 1a | 1b | 1c | 1d | 1e |
| Silicone elastomer NSE in solvent blend | 32.0 | 32.0 | — | — | — |
| Silicone elastomer DSE in solvent blend | — | — | 32.0 | 32.0 | — |
| KSG-18A ®: Dimethicone/phenyl vinyl dimethicone crosspolymer (10 to 20%) in diphenylsiloxy phenyl from Shin Etsu | — | — | — | — | 32.0 |
| Sunflower seed oil | 3.0 | 5.0 | 3.0 | 5.0 | 1.2 |
| Agarose 3% aqueous shear gel | 13.7 | | | | |
| Glycerine | 3.0 | | | | |
| Tween ® 40 | 2.0 | | | | |
| Dimethicone 50 cst | 2.6 | | | | |
| Dimethicone 5 cst | 1.0 | | | | |
| Water and other minor ingredients | To 100 wt % | | | | |

TABLE 2

| Ingredients | Composition Ref Code and wt % | | | |
|---|---|---|---|---|
| | 2a | 2b | 2c | 2d |
| Silicone elastomer NSE in solvent blend | 32.0 | 32.0 | — | — |
| Silicone elastomer DSE in solvent blend | — | — | 32.0 | 32.0 |
| *Macadamia* oil (Floramac ® *Macadamia* Oil Refined from Floratech) | 3.0 | 5.0 | 3.0 | 5.0 |
| Agarose 3% aqueous shear gel | 13.7 | | | |
| Glycerine | 3.0 | | | |
| Tween ® 40 | 2.0 | | | |
| Dimethicone 50 cst | 2.6 | | | |
| Dimethicone 5 cst | 1.0 | | | |
| Water and other minor ingredients | To 100 wt % | | | |

In order to determine whether the compositions were stable or not (upon storage under varying conditions), certain tests were performed. Details thereof are described hereinafter.

Amplitude Sweep Rheology Analysis

DV-II PRO Digital Viscometer (from Brookfield Ltd) was used to measure the viscosities of the roll on samples at a consistent shear rate of 10 rpm. This viscometer was connected with PC where an automate program can control the measurement. The values measured after 1 min at a temperature of 25° C. was used. Values are quoted in centipoises (cP=mPa·S) unless otherwise specified.

Stability Test

Stability, as used herein, refers to the concerned composition maintaining its appearance, odor and main structure without phase separation. Samples of the compositions were poured into plastic bottles and filled up to ⅔ of the bottles. Then the samples were stored at 50° C. in an oven. For stability test, samples were checked daily. The appearance of samples was observed and recorded. The observation was taken when the samples were still warm and then the samples were left in the oven for 24 hours before another observation was taken.

The observations pertaining to the compositions of Table 1 (sunflower seed oil) are tabulated in Table 3. The observations pertaining to the compositions of Table 2 (macadamia oil) are tabulated in Table 4.

TABLE 3

| | | Stability | |
|---|---|---|---|
| Reference Code | Viscosity/cP | 25° C. (12 weeks) | 50° C. (10 weeks) |
| 1a | 14500 | Unstable | Unstable |
| 1b | 14940 | Unstable | Unstable |
| 1c | 14240 | Stable | Stable |
| 1d | 15940 | Stable | Stable |
| 1e | 16550 | NM | Unstable |

NM means that the data was not measured.

TABLE 4

| Reference Code | Viscosity/cP | Stability 50° C. (3 weeks) |
|---|---|---|
| 2a | 16300 | Unstable |
| 2b | 15800 | Unstable |
| 2c | 15800 | Stable |
| 2d | 16250 | Stable |

The unstable formulations are observed as having phase separation (with oil release) while the stable formulation appeared as without any phase separation. It can be seen from the results that samples comprising functional silicone elastomer are more stable compared to the sample comprising non-functional silicone elastomer, which also indicates the functional silicone elastomers can stabilize non-hydrocarbon oil emollient, better than non-functional silicone elastomers. It shows that compositions comprising dual functional (alkyl and phenyl modified) silicone elastomer (as in Formula IV) are more stable than those comprising the non-functional elastomer (with R1, R2, R3=CH3 in Formula 1).

For samples comprising functional silicone elastomers, it further shows that samples comprising DSE are more stable than commercial phenyl modified silicone elastomer/solvent blend (KSG-18A).

The invention claimed is:

1. A cosmetic composition comprising:
   (i) 1 to 30 wt % of a non-hydrocarbon emollient; and
   (ii) 2 to 60 wt % of a blend of dual (alkyl and phenyl) modified silicone elastomer of the Formula (IV) and solvent;
   wherein the solvent for the silicone elastomer is selected from cyclic or linear polydimethylsiloxanes;
   wherein the w/w ratio of the amount of the non-hydrocarbon emollient to the combined amounts of the silicone elastomer and said solvent is from 1:50 to 1:1 and where the amount of the non-hydrocarbon emollient is less than the amount of the silicone elastomer;

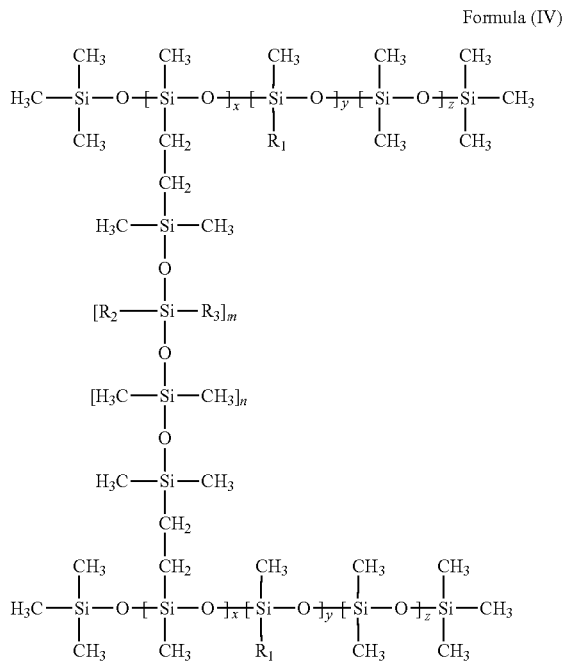

Formula (IV)

wherein:
each $R_1$ is independently, $C_{4-36}$ alkyl chain;
each $R_2$ is independently, phenyl or $CH_3$;
each $R_3$ is independently phenyl; and
each x is independently an integer from 3 to 100; each y is independently an integer from 1 to 100; each z is independently an integer from 1 to 100; each m is independently an integer from 1 to 100; and each n is independently an integer from 4 to 1000,
and wherein the composition comprises less than 2 wt % capric caprylic triglycerides and less than 5 wt % crosslinked elastomeric silicone polyether, wherein said non-hydrocarbon emollient is an alkenyl or alkyl ester of a $C_{10-20}$ fatty acid, an ether-ester, a polyhydric alcohol ester, a wax ester, a mono-, di- or triglyceride, a sterol ester, a fatty alcohol, a fatty acid, lanolin, a phospholipid, beeswax or a sterol, further wherein said triglyceride is one or more of wheatgerm oil, apricot kernel oil, avocado oil, sunflower seed oil, arnica oil, evening primrose oil, jojoba oil, coconut oil, palm kernel oil, groundnut oil, safflower oil, cotton seed oil, rape seed oil, palm oil, almond oil, rice bran oil, castor oil, macadamia oil, shea butter or theobroma oil (cocoa butter).

2. The composition according to claim 1, wherein said cyclic polydimethylsiloxane is octamethylcyclotetrasiloxane, decamethylcyclopentasiloxane or dodecamethylcyclohexasiloxane.

3. The composition according to claim 1, wherein said linear polydimethylsiloxane is trimethicone or dimethicone.

4. The composition according to claim 1, comprising 2 to 10 wt % of the non-hydrocarbon emollient.

5. The composition according to claim 1, wherein the $R_1$ of the silicone elastomer is a $C_{8-12}$ alkyl group.

6. The composition according to claim 1, wherein the $R_2$ of the silicone elastomer is a phenyl group.

7. The composition according to claim 1, wherein alkyl mole content of the silicone elastomer is from 0.01 to 0.99, where alkyl mole content means the ratio of moles of alkyl substituted dimethicone units to the total moles of dimethicone units per mole of silicone elastomer unit.

8. The composition according to claim 1, wherein phenyl mole content of the silicone elastomer is from 0.01 to 0.50, where phenyl mole content means the ratio of moles of phenyl substituted dimethicone units to the total moles of dimethicone units per mole of silicone elastomer unit.

9. The composition according to claim 1, wherein the silicone elastomer and the solvent for said silicone elastomer are present in the form of a blend of which the silicone elastomer forms 1 to 70 parts by weight.

10. A method of moisturizing the skin comprising a step of topically applying a cosmetic composition of claim 1 to the skin.

11. The method of moisturizing the skin according to claim 10, wherein said method is non-therapeutic.

12. The method of moisturizing the skin according to claim 10, wherein the composition further comprises one or more organic sunscreens.

13. The method of moisturizing the skin according to claim 10, wherein the composition further comprises a skin-lightening agent.

14. The composition according to claim 1, wherein in each $R_1$ is independently, $C_{8-18}$ alkyl chain.

15. The composition according to claim 1, wherein each x is independently an integer from 3 to 20; each y is independently an integer from 1 to 20; each z is independently an integer from 6 to 50; each m is independently an integer from 5 to 30; and each n is independently an integer from 40 to 500.

* * * * *